United States Patent
Schuele

(10) Patent No.: US 9,402,692 B2
(45) Date of Patent: Aug. 2, 2016

(54) HEAD FIXATION DEVICE AND APPARATUS FOR SECURING COMPONENTS THERETO

(71) Applicant: Matthias E. Schuele, Freiburg (DE)

(72) Inventor: Matthias E. Schuele, Freiburg (DE)

(73) Assignee: pro med instruments GmbH, Freiburg IM Breisgau (DE)

( * ) Notice: Subject to any disclaimer, the term of this patent is extended or adjusted under 35 U.S.C. 154(b) by 711 days.

(21) Appl. No.: 13/633,164

(22) Filed: Oct. 2, 2012

(65) Prior Publication Data
US 2013/0081636 A1    Apr. 4, 2013

Related U.S. Application Data

(60) Provisional application No. 61/542,246, filed on Oct. 2, 2011.

(51) Int. Cl.
*A61G 15/00*    (2006.01)

(52) U.S. Cl.
CPC .......... *A61B 90/57* (2016.02); *A61B 2090/3983* (2016.02)

(58) Field of Classification Search
CPC ........... A61B 17/2927; A61B 17/1285; A61B 18/1445; A61B 2017/2944; A61B 2017/2945; A61B 2018/1432; A61B 2018/145; A61B 2018/1861; A61B 17/0293; A61B 17/0469; A61B 17/062; A61B 17/064; A61B 17/12; A61B 19/203; A61G 13/12; A61G 13/121; A61G 2013/0054; A61G 2210/50; A61G 2200/325; A61G 13/1295; A61G 15/125; A61F 9/00736; F16M 11/14; F16M 13/02; F16M 2200/022; G01R 33/34007

USPC ........................................ 128/845; 606/56, 59
See application file for complete search history.

(56) References Cited

U.S. PATENT DOCUMENTS

| | | | |
|---|---|---|---|
| 1,839,726 A | | 1/1932 | Arnold |
| 2,586,488 A | | 2/1952 | Smith |
| 2,594,086 A | | 4/1952 | Smith |
| 3,522,799 A | | 8/1970 | Gauthier |
| 3,835,861 A | | 9/1974 | Kees et al. |
| 4,169,478 A | * | 10/1979 | Hickmann ..................... 606/151 |
| 4,312,336 A | | 1/1982 | Danieletto et al. |
| 4,392,645 A | | 7/1983 | Westphal |
| 4,457,300 A | | 7/1984 | Budde |

(Continued)

FOREIGN PATENT DOCUMENTS

| | | |
|---|---|---|
| EP | 1647237 | 4/2006 |
| WO | WO 97/40764 | 4/2001 |
| WO | WO 02/085187 | 10/2002 |

OTHER PUBLICATIONS

Accessories, Officing Sordina S.p.A.

(Continued)

*Primary Examiner* — Michael Brown
(74) *Attorney, Agent, or Firm* — Frost Brown Todd LLC

(57) ABSTRACT

A head fixation device in the form of a skull clamp comprises an integrated rail for attaching accessories thereto. One or more clamps are configured to engage with the integrated rail. Additional accessories can be attached to the one or more clamps, which also include a starburst interface and an integrated rail. The clamps use a linear translating closure mechanism to engage the clamps to the integrated rail of the skull clamp. In some versions, the head fixation device is configured with a navigation adapter that attaches to an upper portion of the skull clamp.

17 Claims, 15 Drawing Sheets

(56) References Cited

U.S. PATENT DOCUMENTS

| | | |
|---|---|---|
| 4,539,979 A | 9/1985 | Bremer |
| 4,541,421 A | 9/1985 | Iversen et al. |
| 4,543,947 A | 10/1985 | Blackstone |
| 4,615,072 A | 10/1986 | Lautenschlager, Jr. |
| 4,667,660 A | 5/1987 | Eingorn |
| 4,796,846 A | 1/1989 | Meier et al. |
| 4,803,976 A | 2/1989 | Frigg et al. |
| 4,807,605 A | 2/1989 | Mattingly |
| 4,827,926 A | 5/1989 | Carol |
| 4,838,264 A | 6/1989 | Bremer et al. |
| 4,971,037 A | 11/1990 | Pelta |
| 5,203,765 A | 4/1993 | Friddle, Jr. |
| 5,276,927 A | 1/1994 | Day |
| 5,284,129 A | 2/1994 | Agbodoe et al. |
| 5,501,685 A | 3/1996 | Spetzler |
| 5,529,358 A | 6/1996 | Dinkler et al. |
| 5,537,704 A | 7/1996 | Dinkler et al. |
| 5,630,805 A | 5/1997 | Ternamian |
| 5,669,912 A | 9/1997 | Spetzler |
| 5,722,978 A | 3/1998 | Jenkins, Jr. |
| 5,865,780 A | 2/1999 | Tuite |
| 5,891,157 A | 4/1999 | Day et al. |
| 5,954,723 A | 9/1999 | Spetzler |
| 6,110,182 A | 8/2000 | Mowlai-Ashtiani |
| 6,129,729 A | 10/2000 | Snyder |
| 6,198,961 B1 | 3/2001 | Stern et al. |
| 6,306,146 B1 | 10/2001 | Dinkler |
| D456,510 S | 4/2002 | Spetzler et al. |
| 6,598,275 B1 | 7/2003 | Kolody et al. |
| 6,659,972 B2 | 12/2003 | Stamper et al. |
| 6,684,428 B2 | 2/2004 | Grotenhuis et al. |
| 6,805,453 B2 | 10/2004 | Spetzler et al. |
| 7,048,735 B2 | 5/2006 | Ferrante et al. |
| 7,232,411 B2 | 6/2007 | Dinkler, II et al. |
| 7,730,563 B1 | 6/2010 | Sklar et al. |
| 8,287,537 B2 * | 10/2012 | Dinkler, II ............... 606/59 |
| 2007/0250071 A1 * | 10/2007 | Soerensen et al. ........... 606/130 |
| 2010/0059064 A1 | 3/2010 | Schuele et al. |
| 2014/0194734 A1 * | 7/2014 | Birkenbach et al. ......... 600/424 |

OTHER PUBLICATIONS

Codman, "Bookwalter Retractor Kit II", By: Bookwalter, Rochard & Thompson.

European Search Report dated May 11, 2006 for Application No. EP 05292169.

Partial European Search Report dated Feb. 6, 2006 for Application No. EP 05292169.

Screenshots from www.bicakcilar.com, printed Jan. 28, 2005.

Screenshots from www.integra-1s.com, printed Jan. 28, 2005.

Screenshots from www.integra-1s.com, printed Dec. 28, 2005.

Tuite, G., M.D., et al. "Use of an Adjustable Transportable Radiolucent Spinal Immobilization Device in the Comprehensive Management of Cervical Spine Instability", Journal of Neurosurgery, vol. 85(6), Dec. 1996, American Assoc. of Neurosurgeons. Abstract.

European Search Report and Written Opinion dated Jan. 7, 2013 for Application No. EP 12006851.

European Communication dated Feb. 8, 2014 for Application No. EP 12006851.5.

GE Healthcare, Mayfield MR compatible clamp, MR Surgical Suite, available at http://www3.gehealthcare.com/en/products/categories/magnetic_resonance_imaging/mr_surgical_suite#tabs/tab8DDAFB22788244329DF155B67E418F3D, printed Apr. 10, 2015, p. 1-6.

GE Healthcare, Mayfield MR compatible clamp, MR Surgical Suite, available at http://www3.gehealthcare.com/~/media/images/product/product-categories/magnetic-resonance-imaging/mr%20surgical%20suite/mayfield-mr-compatible-clamp.jpg, printed Apr. 10, 2015, p. 1.

\* cited by examiner

HEAD FIXATION DEVICE AND APPARATUS FOR SECURING COMPONENTS THERETO

PRIORITY

This application claims priority to U.S. Provisional Patent Application Ser. No. 61/542,246, filed Oct. 2, 2011, entitled "Apparatus for Securing Components to a Head Fixation Device," the disclosure of which is incorporated by reference herein.

BACKGROUND

In the field of head and neck diagnostics and surgery, there exist a variety of head fixation devices (herein also referred to as "HFDs" or "HFD" in singular) to help stabilize a patient before undergoing a procedure. In some instances it can be useful to attach various other components to the head fixation device being used. While a variety of HFDs and apparatuses used to attach various components to a HFD or other support or stabilizing device have been made and used, it is believed that no one prior to the inventor(s) has made or used an invention as described herein.

BRIEF DESCRIPTION OF THE DRAWINGS

It is believed the present invention will be better understood from the following description of certain examples taken in conjunction with the accompanying drawings, in which like reference numerals identify the same elements.

Figure 1:
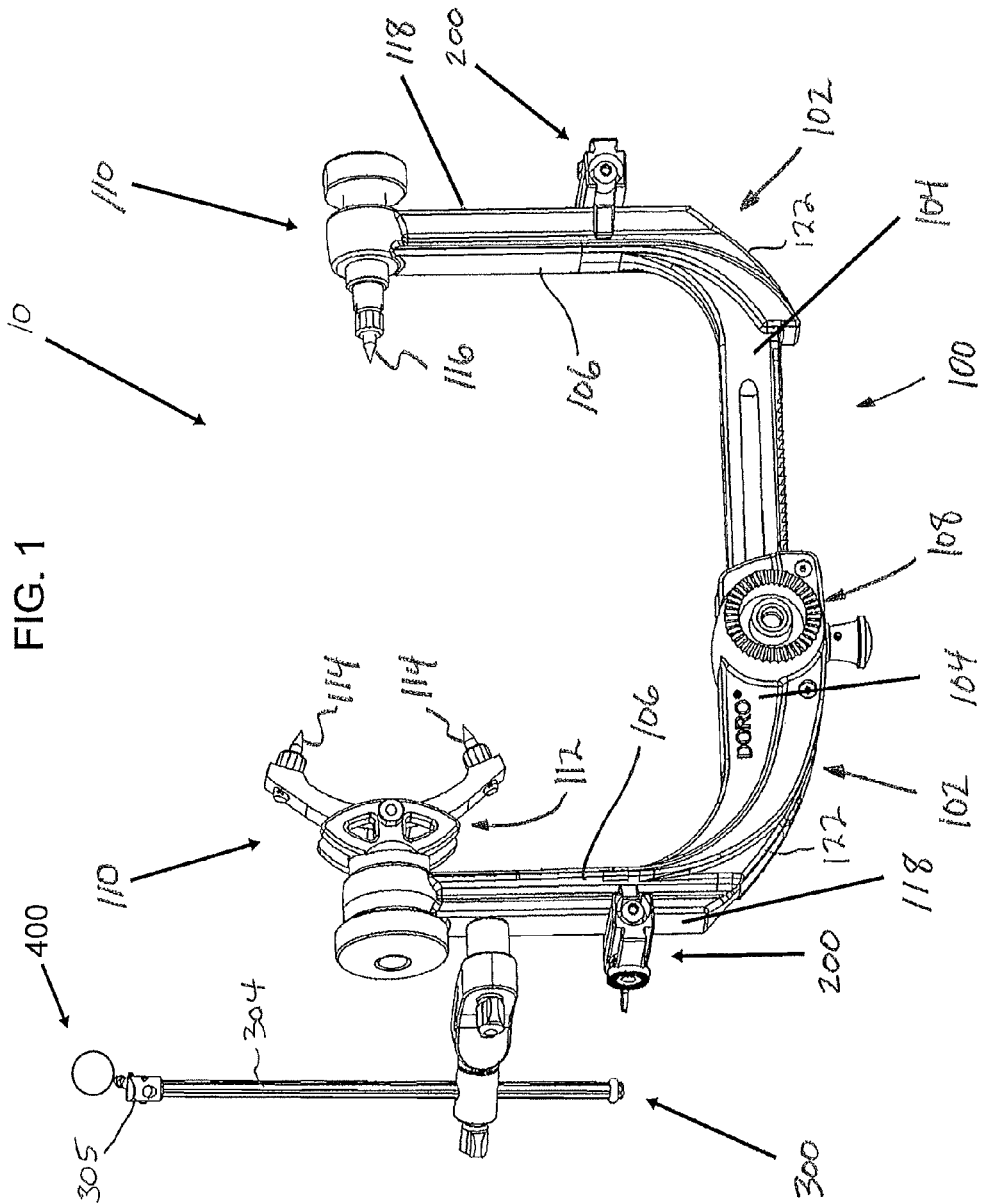
FIG. 1 depicts a perspective view of an exemplary HFD, shown in the form of a skull clamp having two arms adjustable in width, the HFD further shown with two attached quick-clamps (also referred to herein as "clamps" or "clamp" in singular) and one attached navigation adapter.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description. As will be realized, the invention is capable of other different and obvious aspects, all without departing from the invention. Accordingly, the drawings and descriptions should be regarded as illustrative in nature and not restrictive.

FIG. 1 illustrates an exemplary HFD (10) in the form of a skull clamp (100) having two clamps (200) and a navigation adapter (300) attached. The skull clamp (100) itself comprises two arms (102) that each have a lateral portion (104) and an upright portion (106). The lateral portion (104) of one of the arms (102) is configured to receive the lateral portion (104) of the other of the arms (102). In the present example, one of the lateral portions (104) includes a starburst interface (108) for connecting the skull clamp (100) with another structure, e.g., an OR table (not shown). The skull clamp (100) can be connected directly to the OR table or indirectly via, e.g., a position adapter (not shown). At the top of each arm's upright portion (106) is a skull pin assembly (110) that can either be have one or more skull pins connected thereto. In the present example, one upright portion (106) includes a rocker arm (112) with dual skull pins (114), while the other upright portion (106) includes a skull pin assembly (110) having a single skull pin (116).

Exemplary Quick-Rail (Also Referred to Herein as "Rails" or "Rail" in Singular)

Each upright portion (106) of an arm (102) is configured with an integrated rail (118) where the profile of the upright portion (106) defines rail (118). Integrated rail (118) in the present example takes the form of an I-beam or similar form. As will be discussed further below, rail (118) is configured to receive one or more accessories, e.g., navigation adapter (300), clamps (200), or other accessories. As shown in the illustrated version, HFD (10) includes clamp (200) on each rail (118) and navigation adapter (300) on one of rails (118).

Figure 2:
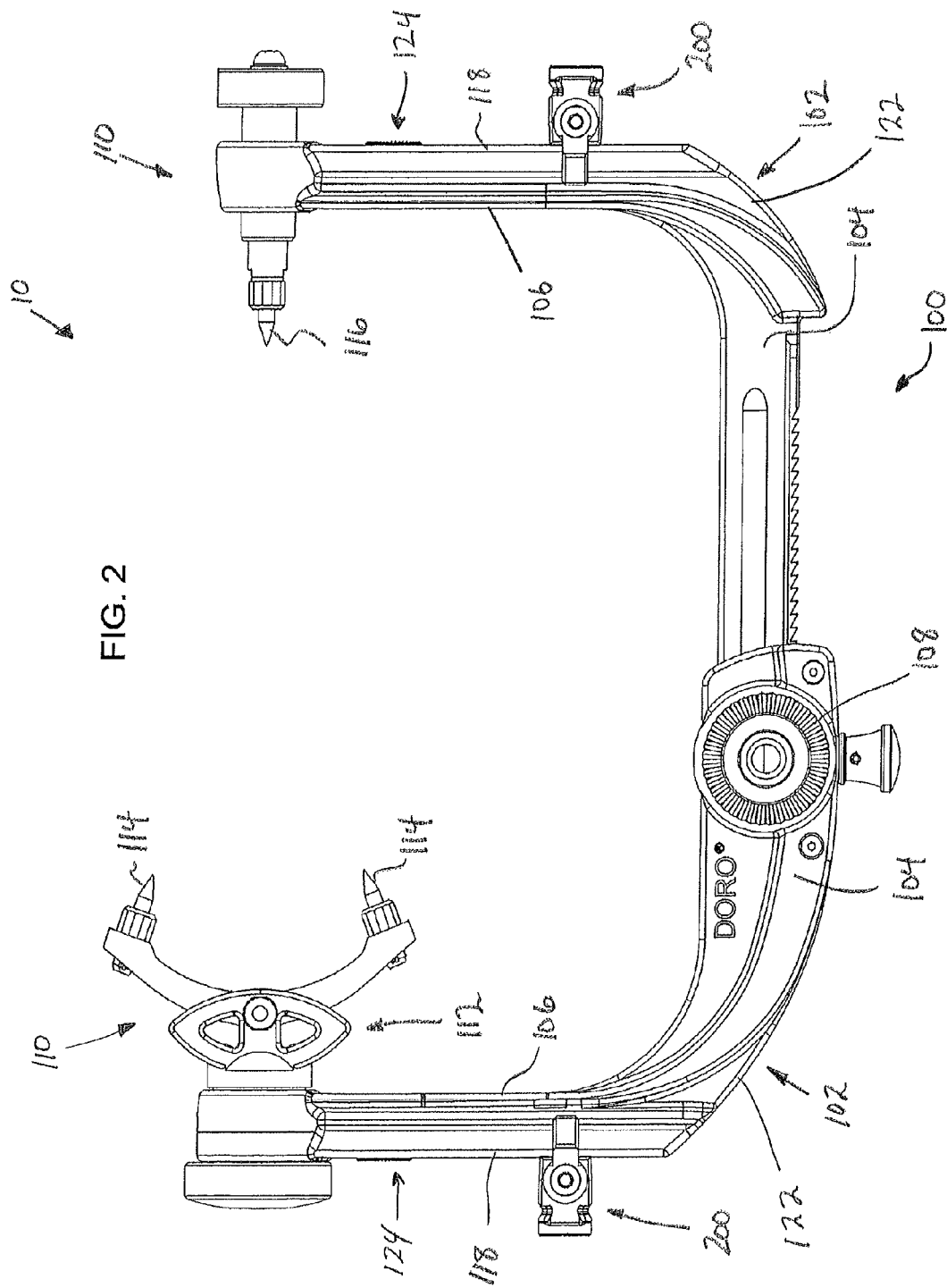
FIG. 2 depicts a rear view of the HFD of FIG. 1, shown without the navigation adapter connected.
Figure 3:
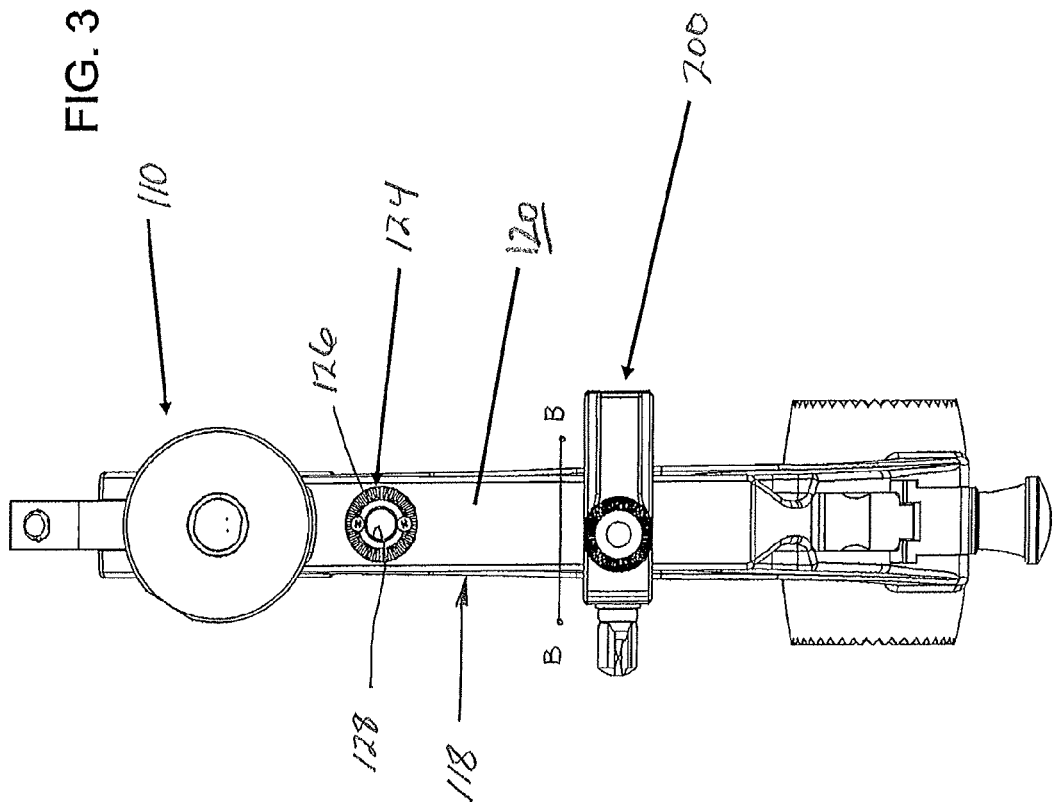
FIG. 3 depicts a side view of the HFD of FIG. 1, shown without the navigation adapter connected.
Figure 4:
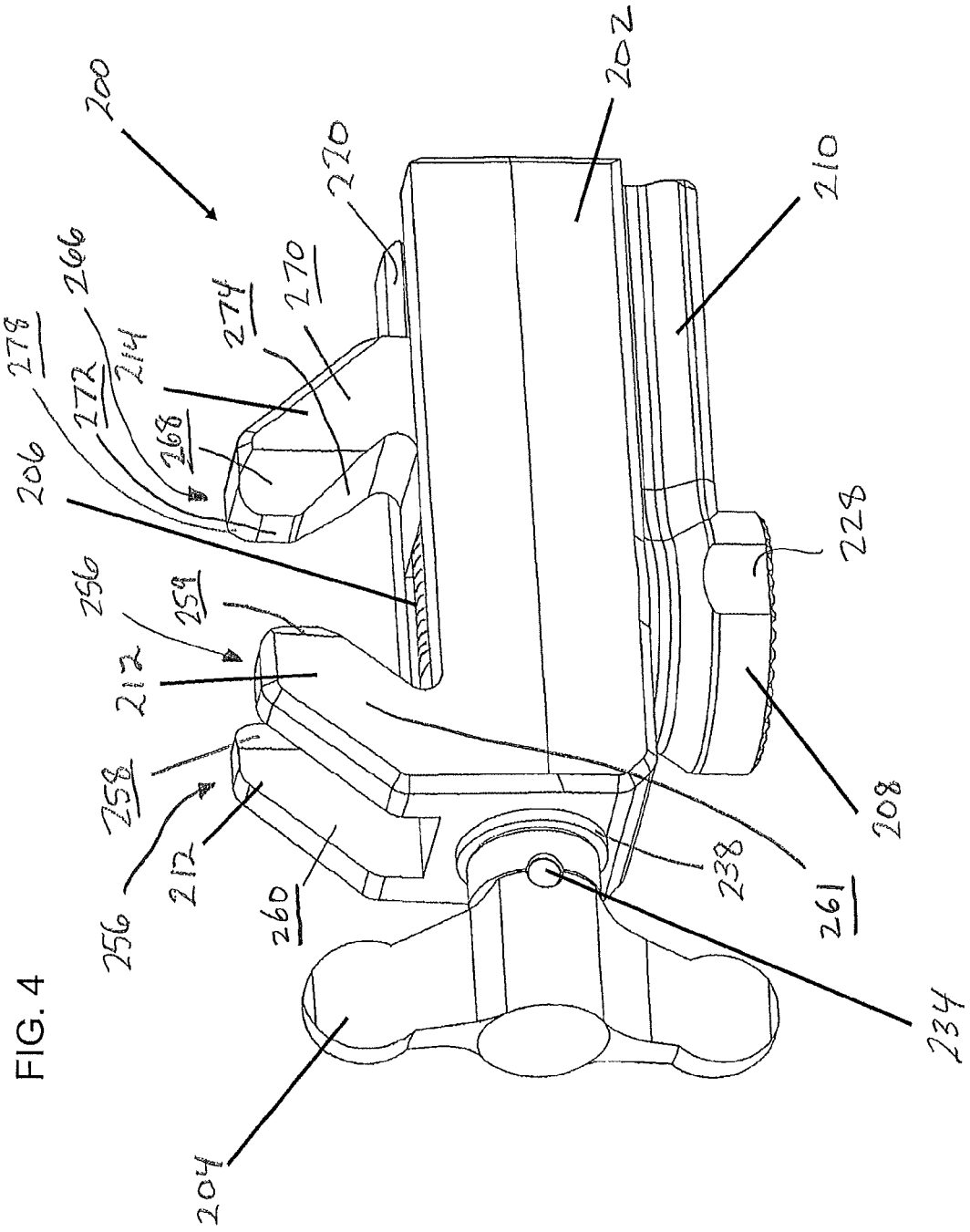
FIGS. 4-6 depict perspective views of an exemplary clamp as shown in FIG. 1.
Figure 5:
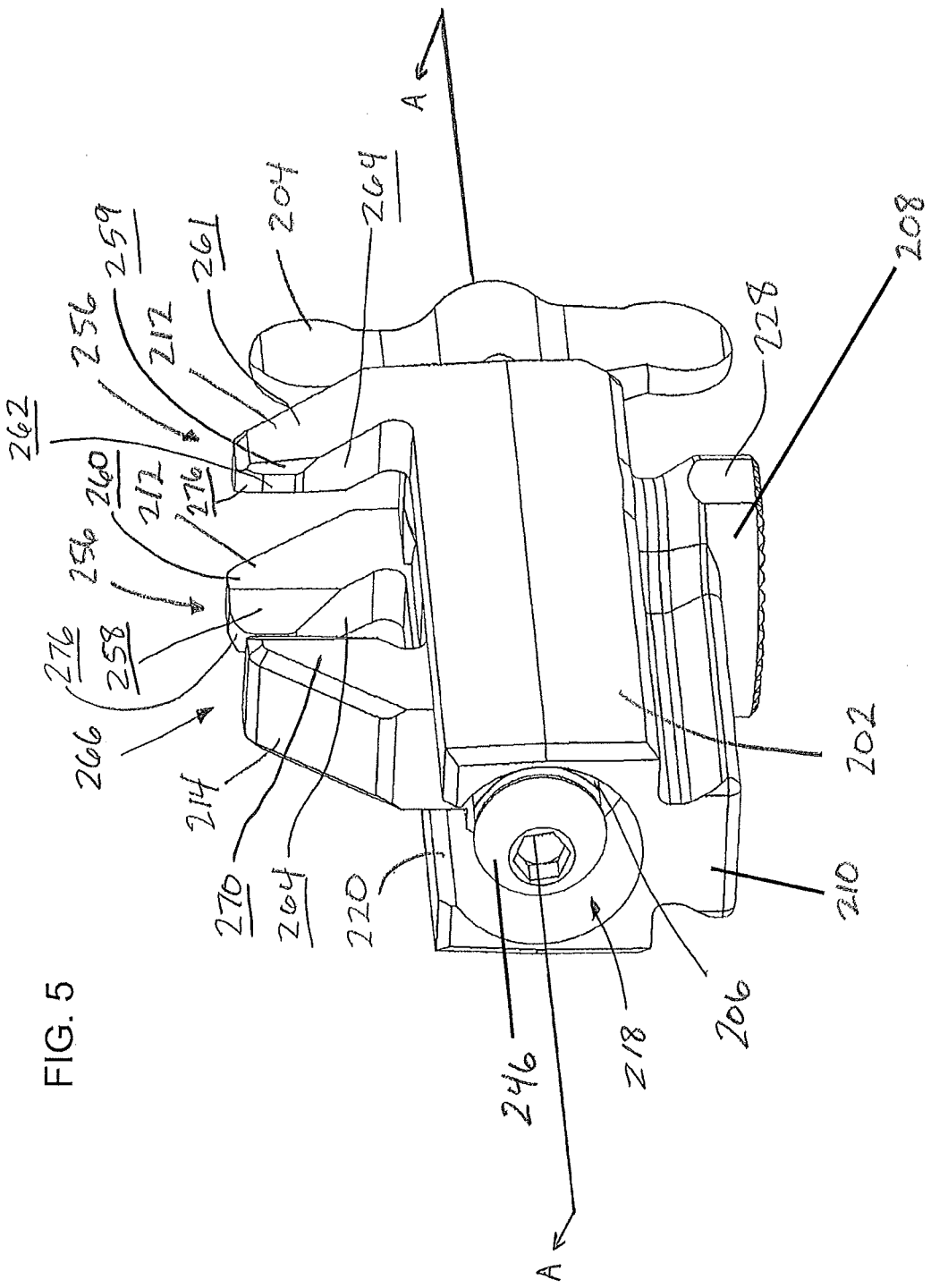
Figure 6:
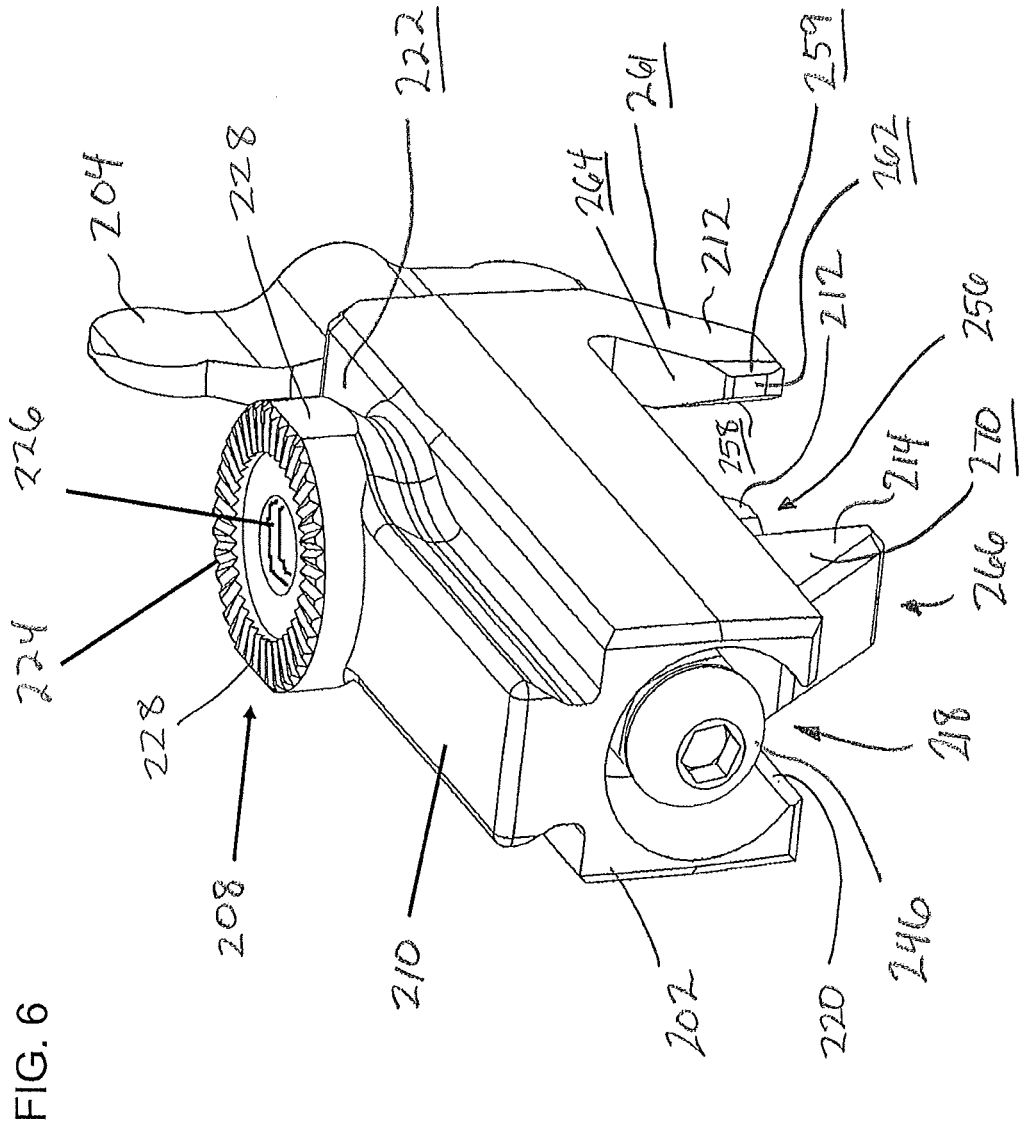
Figure 7:
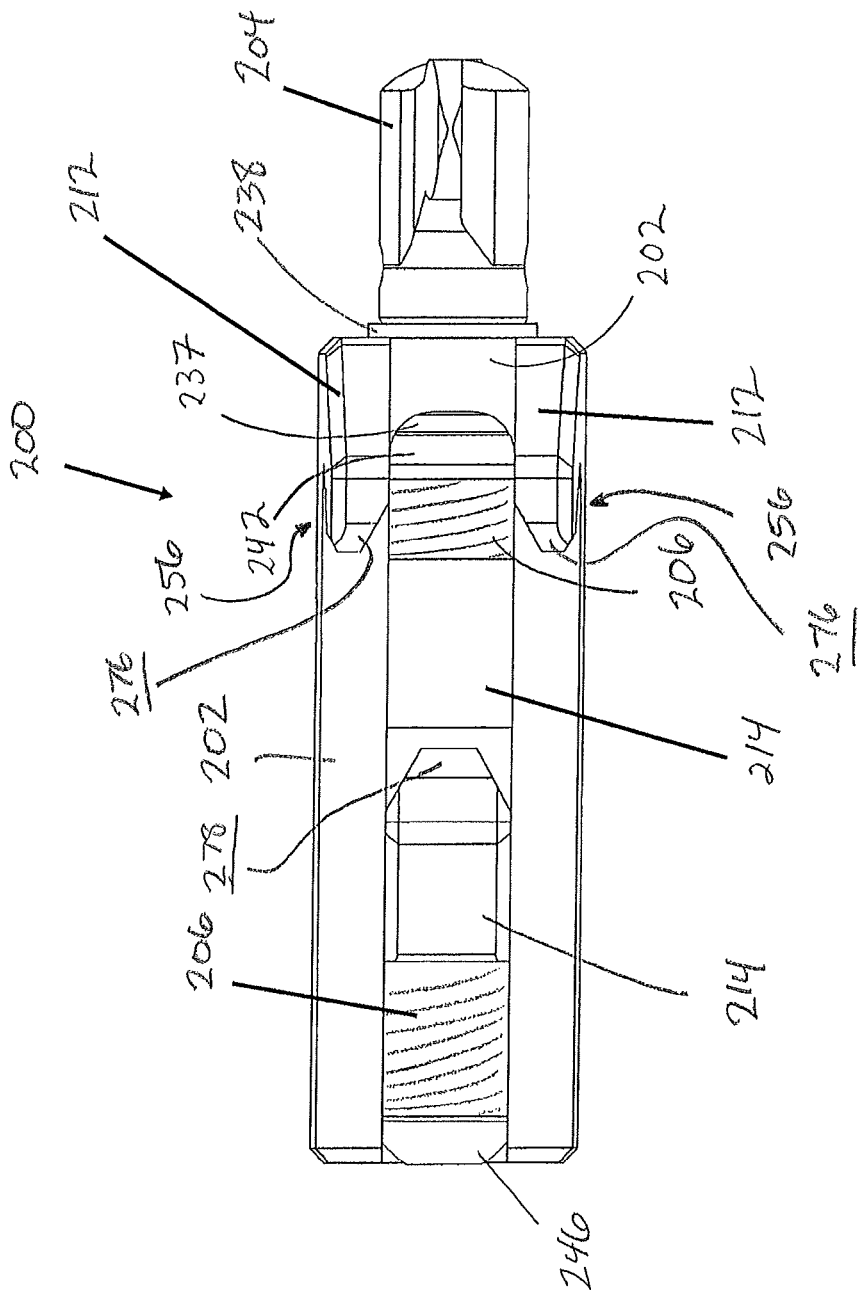
FIG. 7 depicts a side view of the clamp of FIG. 1.

FIGS. 2-3 illustrate HFD (10), but shown without navigation adapter (300) so as to present more details of rails (118) and clamps (200). Rails (118) in the present example have an outer surface (120) with a width of about 25 mm. Of course in other versions, the dimensions of rails (118) can be larger or smaller that those shown and described in the illustrated version. Also, rails (118) are configured as straight in the illustrated version, extending generally along the length of upright portions (106), but generally not extending along the length of transitional curves (122) from upright portions (106) to lateral portions (104), and not extending along lateral portions (104) themselves. Of course in other versions, rails (118) can be configured as curved along any portions of upright portions (106), transitional curves (122), and lateral portions (104).

FIG. 3 illustrates a view that shows rails (118) comprise starburst interface (124) (also referred to at times as a "starburst feature") on outer surface (120) of each rail (118). Starburst interface (124) is configured as an accessory attachment interface such that various accessories or other components can be mounted to starburst interface (124). In the present example, starburst interface (124) is positioned generally near the upper portion of rail (118) below skull pin assemblies (110). In other words, starburst interface (124) is positioned along an upper portion of arm (102) substantially proximal or adjacent to a stabilizing feature that is configured to contact a patient's head, e.g., skull pin assemblies (110) with skull pins (114). Positioning starburst interface (124) near the upper portion of rail (118) allows for starburst interface (124), and whatever accessory is mounted thereto, to be close to the patient's head and/or close to the points where skull clamp (100) connects with or contacts the patient's head. In other words, in the present example, starburst interface (124) is mounted to, connected with, or part of HFD (10) in such a way that starburst interface (124) is close to the patient's head and/or close to the points where the patients head contacts the HFD. In some other versions starburst interfaces (124) can be in other positions along rails (118).

Starburst interfaces (124) comprise teeth (126) that extend in a circular fashion, where teeth (126) are configured to engage teeth of a complementary starburst interface, e.g. the complementary starburst interface on navigation adapter (300) as will be described further below. Starburst interfaces (124) on rail (118) further comprise threaded bore (128) near the center, where threaded bore (128) is configured to engage a bolt, screw, or rod having corresponding threads, where the bolt, screw, or rod can be a component of the complementary starburst interface. In the present example, starburst interface (124) on rail (118) is used as a connection point for navigation adapter (300). Of course any variety of accessories could be used with starburst interface (124).

Exemplary Clamp

FIGS. 4-8 illustrate one of clamps (200) depicted in FIG. 1, the other clamp (200) having the same structure and function. In the present example, clamp (200) comprises a body (202), an actuator (204) in the form of a winged member, a threaded rod (206), a starburst interface (208), a rail (210), dual stationary jaws (212) that are formed integral with body (202), and a single movable jaw (214). In using clamp (200), rotating actuator (204) turns threaded rod (206) in place. Single movable jaw (214) comprises a threaded bore (216) positioned about threaded rod (206) such that the threads of threaded bore (216) engage the threads of threaded rod (206). When actuator (204) is rotated, movable jaw (214) is prevented from rotating based on the configuration of body (202), which comprises a channel (218) that houses threaded rod (206), and body (202) also includes sidewalls (220) that contact movable jaw (214) to prevent it from rotating. Without the ability to rotate in unison with threaded rod (206) and actuator (204), movable jaw (214) translates linearly along threaded rod (206) in response to rotation of actuator (204) based on the engagement between threaded rod (206) and threaded bore (216).

Figure 8:
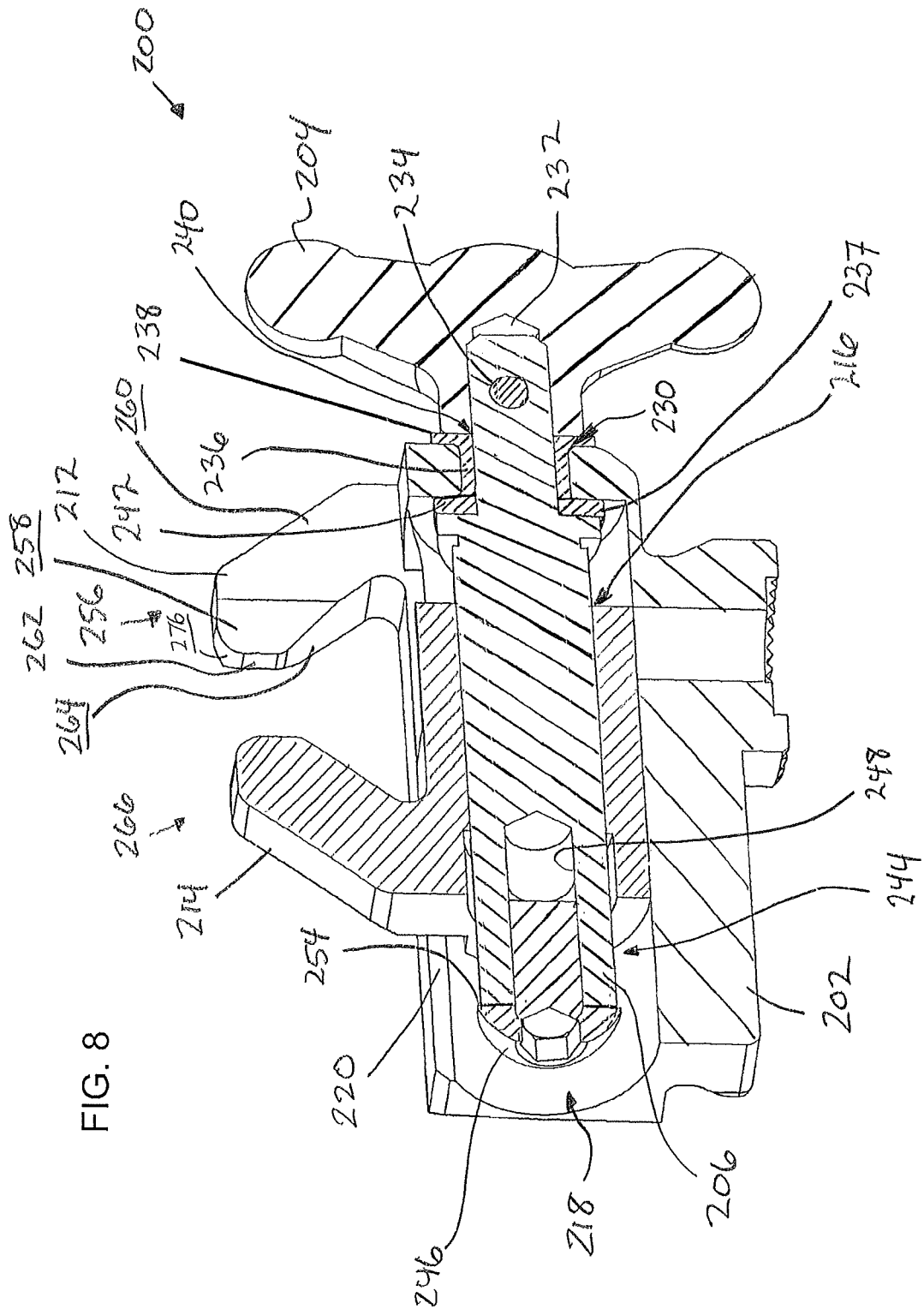
FIG. 8 depicts a perspective view of the clamp of FIG. 1, shown in cross section, the cross section taken along line A-A as seen in FIG. 5.

As illustrated in FIG. 8, body (202) comprises bore (230) through which threaded rod (206) extends. Actuator (204) comprises bore (232), pin (234), collar (236), and washer (237). Collar (236) comprises flange (238) that is positioned adjacent the outer surface of body (202) around bore (230). The remainder of collar (236) generally fits within bore (230). Washer (237) is positioned adjacent the inner surface of body (202) around bore (230). Collar (236) further comprises bore (240) such that bore (230) of body (202) and bore (240) of collar (236) are generally concentric. Threaded rod (206) extends through bores (230, 240, 232) and pin (234) extends laterally through actuator (204) and through an end portion of threaded rod (206) to retain threaded rod (206) within actuator (204). As also illustrated in FIG. 8, threaded rod (206) comprises flange (242) that generally is adjacent washer (237) within body (202). This configuration described above allows for threaded rod (206) and actuator (204) to rotate in unison, and also allows actuator (204) and threaded rod (206) to maintain their lateral positions relative to body (202) such that when rotated, threaded rod (206) and actuator (204) rotate in place and do not translate laterally. In some versions, in addition to being retained by pin (234), bore (232) of actuator (204) is threaded and engages the end of threaded rod (206) with a threaded engagement. Once pin (234) is placed, in such versions, rotation of actuator (204) cannot cause the threaded engagement of actuator (204) and threaded rod (206) to be undone.

As also illustrated in FIG. 8, in some versions threaded rod (206) comprises end (244) opposite the end of threaded rod (206) that joins with actuator (204). End (244) is configured with threaded bore (248) to accept screw (246) that has complementary threads. Screw (246) is sized such that a lip (254) extends past the diameter of threaded rod (206). Lip (254) is sized such that it is slightly larger than the diameter of bore (216) of movable jaw (214) such that when clamp (200) is opened fully, the end of movable jaw (214) abuts lip (254) of screw (246) thereby retaining movable jaw (214) within body (202).

Positioned on an outer surface (222) of clamp (200) is starburst interface (208) and rail (210). In the present example, rail (210) merges with starburst interface (208). Both rail (210) and starburst interface (208) on clamp (200) provide locations for attaching other components or accessories, e.g., retractors, etc. Starburst interface (208) on clamps (200) comprises teeth (224) that surround a central threaded bore (226). Teeth (224) and threaded bore (226) are configured to engage with a complementary starburst interface the same or similar to those described above. Starburst interface (208) positioned on clamp (200) also comprises sides (228) having flat surfaces.

Figure 9:
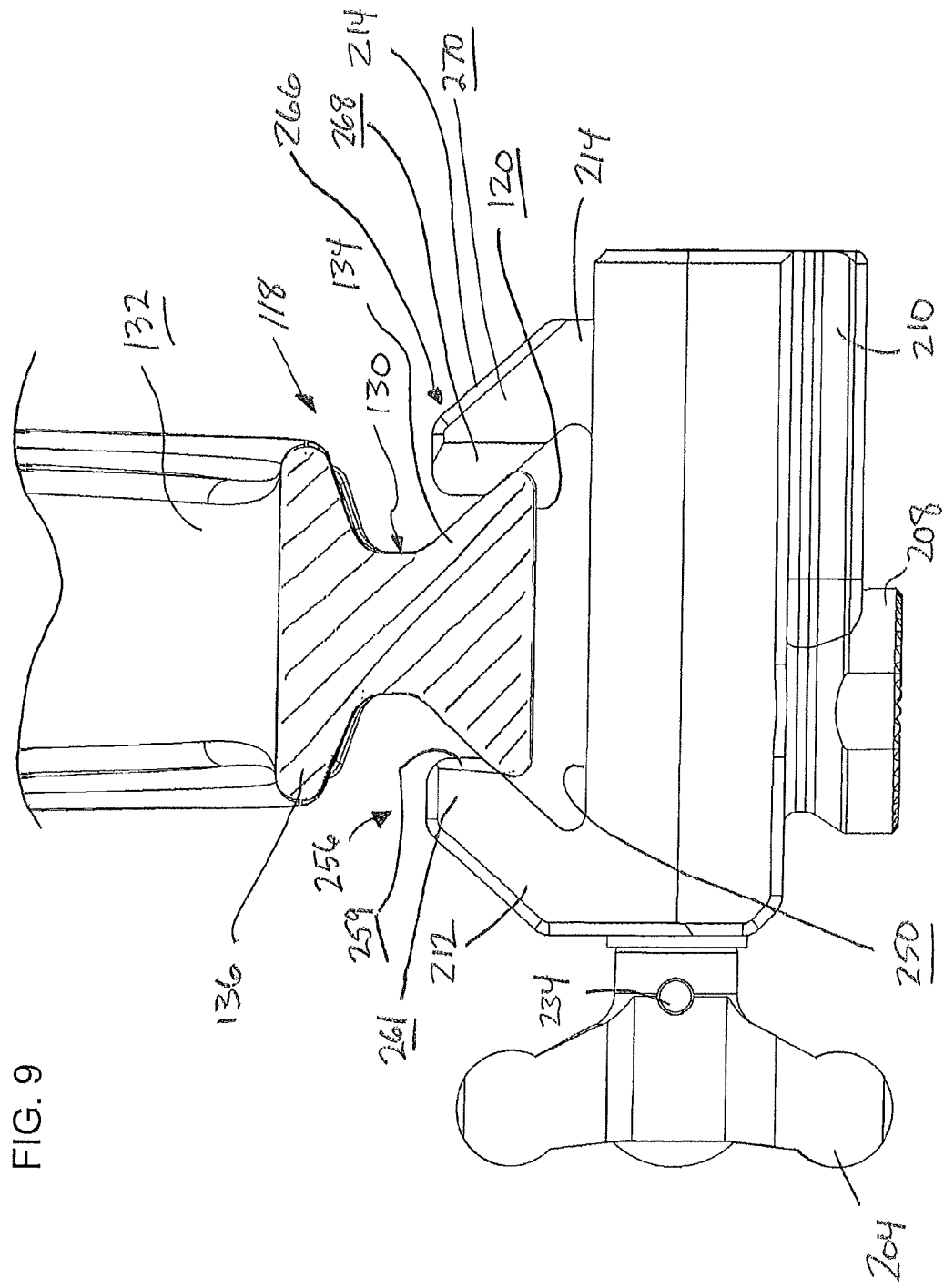
FIGS. 9 and 10 depict a series of top views, shown in cross section, of the clamp of FIG. 1, showing the clamp connecting to the HFD at different points in the connection process, the cross section made just above the clamp point of attachment to the HFD along line B-B as seen in FIG. 3; the series of drawings showing how the clamp draws closer to the outer surface of the HFD arm and integrated rail as the clamp is tightened.
Figure 10:
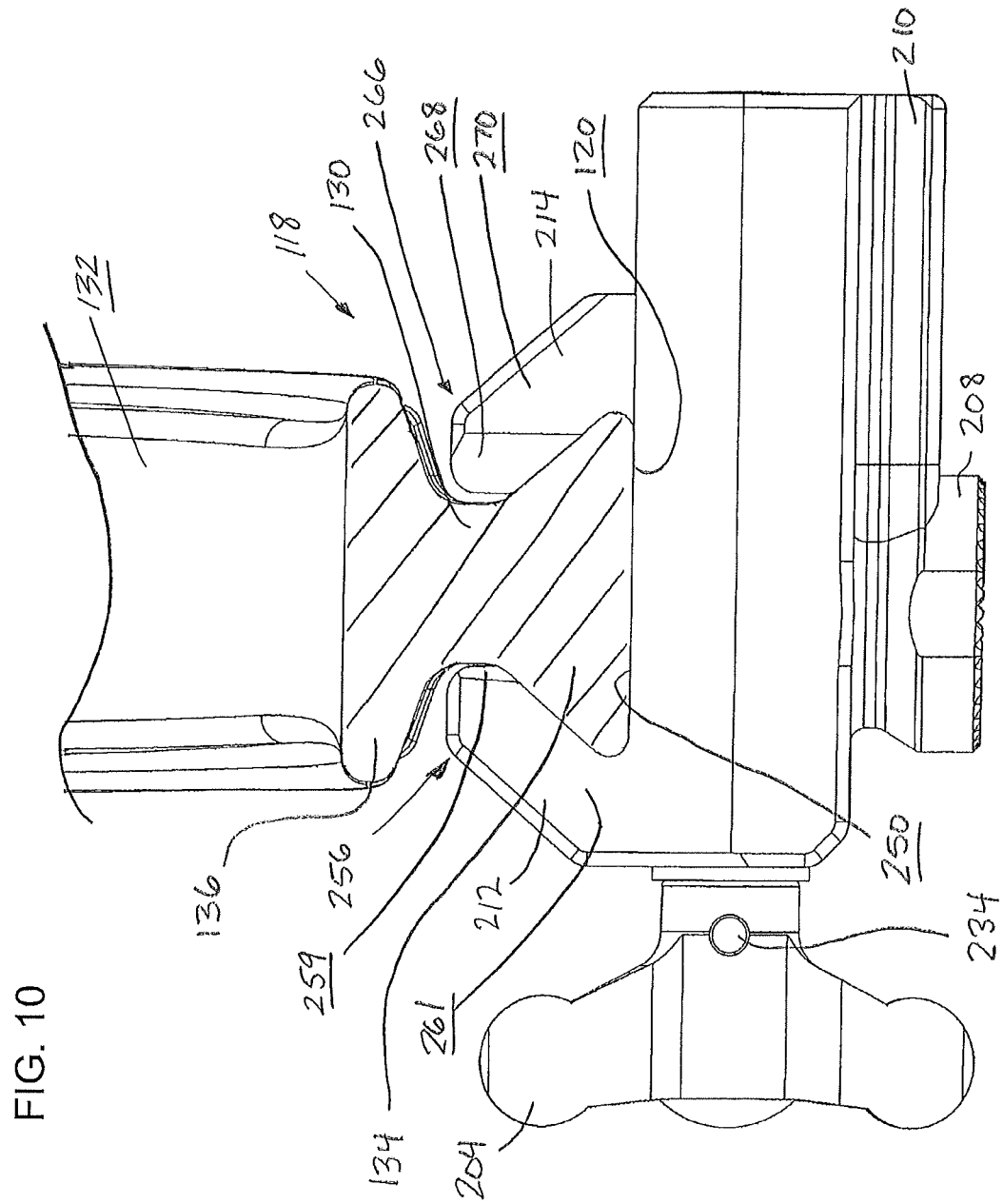
Figure 11:
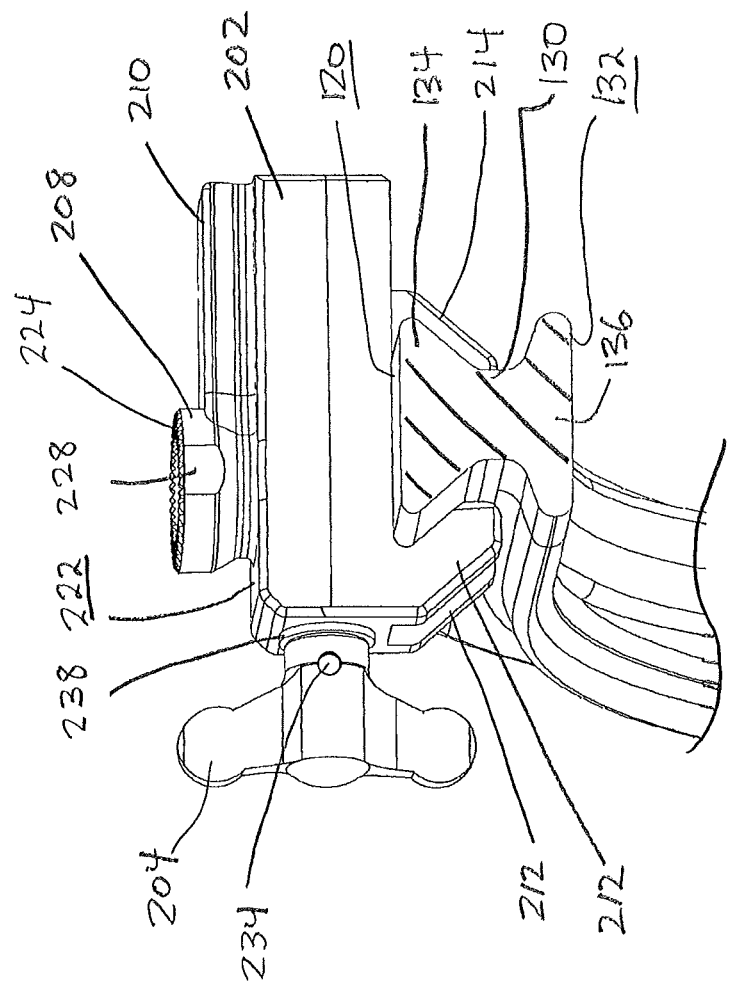
FIG. 11 depicts a perspective view, shown in cross section, of the clamp connected to the HFD as shown in FIG. 10, the cross section again made just above the clamp point of attachment to the HFD.

FIGS. 9 and 10 illustrate a sequence of attaching clamp (200) to rail (118) and also illustrate the cross section profile of arms (102) and integrated rails (118) as well as the void space or shape defined by jaws (212, 214) of clamp (200). As can be seen from the successive views, as clamp (200) is tightened, the complementary profile of rail (118) and that defined by jaws (212, 214) of clamp (200) causes clamp (200) to draw itself closer and closer to outer surface (120) of rail (118). This continues until outer surface (120) of rail (118) substantially contacts an inner surface (250) of clamp (200). In this position, as shown in FIGS. 9-11, clamp (200) provides at least a general four-point security or fixation, with each of two stationary jaws (212) contacting rail (118), one movable jaw (214) contacting rail (118), and inner surface (250) of clamp (200) contacting outer surface (120) of rail (118).

It should be understood that when describing any number of "points of fixation," fixation along points of contact is included as well as fixation along surfaces of contact. It should also be understood that at least four-point security or fixation means four or more points of fixation. Similarly, at least three points of fixation or at least three-point fixation means three or more points of fixation.

In some versions, dual jaws (212) can be replaced with a single jaw (212). FIGS. 9 and 10 are applicable to depict a two total jaw configuration with one fixed jaw (212) and one movable jaw (214). In some versions, clamp (200) provides at least a general three-point security or fixation. This may include fixation at the ends of a three jaw system, or fixation at the ends of a two jaw system with also contact along inner surface (250) of clamp (200) and outer surface (120) of rail (118). In view of the teachings herein, other configurations of jaws (212, 214) and surfaces (120, 250) of clamp (200) and rail (118) to achieve at least three point fixation will be apparent to one of ordinary skill in the art.

As mentioned above arms (102) of skull clamp (100) have integrated rails (118). As best seen in the cross sections of FIGS. 9-11, rails (118) have a generally I-beam like profile. More specifically, each rail (118) comprises outer surface (120), inner surface (132), and middle portion (130). Middle portion (130) is a narrow width portion of rail (118) and extending from each side of middle portion (130) are outer protrusion (134) and inner protrusion (136) respectively. In the illustrated version, protrusions (134, 136) generally have a triangular dovetail-like shape. More specifically, however, protrusions (134, 136) do not have identical shapes as seen in the illustrated version. Of course in some other versions protrusions (134, 136) can have identical shapes. In the present example, inner surface (132) has a greater width than outer surface (120) such that inner protrusion (136) has a greater width than outer protrusion (134). Also, the distance from the center point of middle portion (130) to inner surface (132) is less than the distance from the center portion of middle portion (130) to outer surface (120). This difference in distances contributes to inner protrusion (136) having a flatter profile where it extends a lesser distance from middle portion (130) compared to outer protrusion (134), which has a less flat profile and extends a greater distance from middle portion (130). Referring to FIGS. 10 and 11, it is shown that in the present example, when jaws (212, 214) of clamp (200) are fully engaged with rail (118), the void space or shape defined by jaws (212, 214) matches the profile of outer protrusion (134) of rail (118) such that clamp (200) securely engages rail (118). Stated another way, the shape defined by jaws (212, 214) of clamp (200) is adjustable and can be configured to substantially match, or even exactly match, the cross sectional profile of the structure jaws (212, 214) are being mounted to.

Referring again to FIGS. 4-8, jaws (212) comprise ends (256). Ends (256) each comprise tapered surfaces (258, 259) on each side of each jaw (212), where tapered surfaces (258) extend outwardly from inner surfaces (260) on each side of each jaw (212) to end surfaces (262) of jaws (212). Similarly tapered surfaces (259) extend inwardly from outer surfaces (261) on each side of each jaw (212) to end surfaces (262) of jaws (212). Jaws (212) further comprise inclined surfaces (264) that are configured to contact outer protrusion (134) when clamp (200) is engaged with rail (118). End surfaces (262) extend outwardly away from threaded rod (206) in a generally perpendicular fashion. When clamp (200) is fully engaged with rail (118), end surfaces (262) are generally adjacent to middle portion (130) of rail (118).

Similar to jaws (212), jaw (214) comprises end (266). End (266) comprises tapered surfaces (268) on each side of jaw (214), where tapered surfaces (268) extends inwardly from outer surfaces (270) of jaw (214) to end surface (272) of jaw (214). Jaw (214) further comprises inclined surface (274) that is configured to contact outer protrusion (134) when clamp (200) is engaged with rail (118). End surface (272) extends outwardly away from threaded rod (206) in a generally perpendicular fashion. When clamp (200) is fully engaged with rail (118), end surface (272) is generally adjacent to middle portion (130) of rail (118).

In some versions, rail (118) is sized such that end surfaces (262, 272) contact middle portion (130) of rail when clamp (200) is fully engaged with rail (118). In such versions, clamp (200) maintains generally at least a seven point security or fixation with rail (118) via contact between: (a) rail (118) and each of three end surfaces (262, 272) of jaws (212, 214), (b) rail (118) and each of three inclined surfaces (264, 274) of jaws (212, 214), and (c) rail (118) and inner surface (250) of clamp (200). Also, in some versions jaw (214) can be replaced by a component having two jaw members instead of one such that clamp (200) comprises a total of four jaws. In view of the teachings herein, other modifications to clamp (200) and jaws (212, 214) will be apparent to those of ordinary skill in the art.

Figure 12:
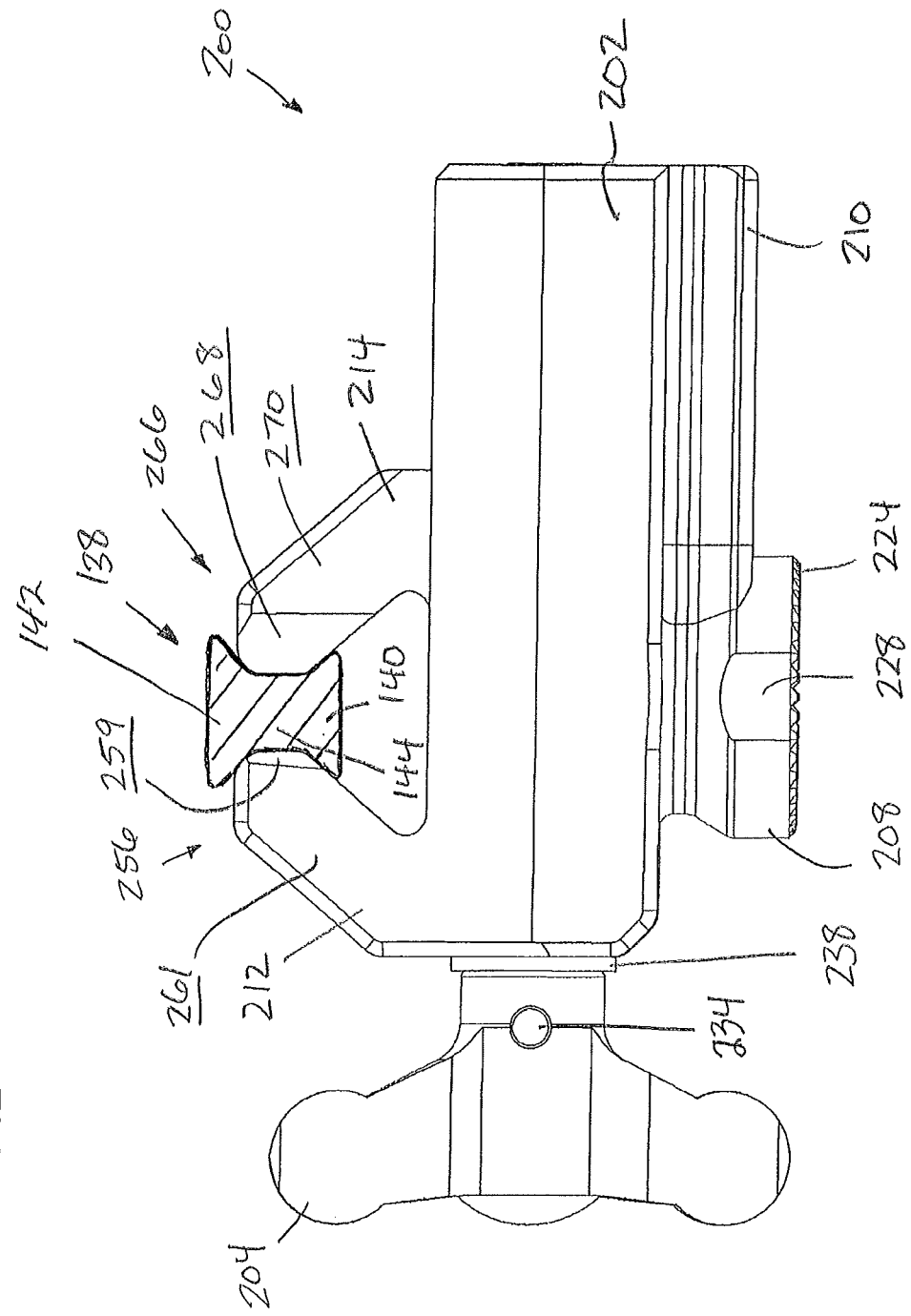
FIG. 12 depicts a top view of the clamp connected to a smaller rail shown in cross section, showing that the clamp is compatible with rails of various sizes.

FIG. 12 illustrates an exemplary version where clamp (200) as described above, is used with, and compatible with, a smaller rail (138). In this version, because rail (138) has a smaller size, outer surface (140) of rail (138) does not contact inner surface (250) of clamp (200) when clamp (200) is secured to rail (138). However, there continues to be secure fixation because each of three jaws (212, 214) of clamp (200) contact rail (138) at at least two points along the profile of rail (138). For instance, in the illustrated version, rail (138) has an I-beam profile generally, and when secured, each jaw (212, 214) of clamp (200) contacts at least two portions of rail (138). For instance, contact is made along an outer protrusion (140) of rail (138) and along an inner protrusion (142) of rail (138). In some versions, contact can also be made along the sides of middle portion (144) of rail (138). As shown in the illustrated version, clamp (200) maintains at least nine points of security or fixation with rail (138) as shown by contact between: (a) rail (138) and each of three end surfaces (262, 272) of jaws (212, 214), (b) rail (138) and each of three inclined surfaces (264, 274) of jaws (212, 214), and (c) rail (138) and each of three upper surfaces (276, 278) of jaws (212, 214). Stated another way, in some versions, ends (256, 266) of jaws (212, 214) are shaped to match the void space defined by the cross sectional profile of rail (138). It should further be noted that in some versions, dual jaws (212) may be replaced by a single jaw (212) for an overall two jaw system used with rail (138). Furthermore, in some versions, single jaw (214) may be replaced by a dual jaw configuration to provide an overall four jaw system used with rail (138). In view of the teachings herein, other ways to modify clamp (200) and rails (118, 138) such that clamp (200) will function with rails of various sizes and/or shapes will be apparent to those of ordinary skill in the art.

With the configuration of clamp (200) and rail (118) as described above, an automatic alignment of clamp (200) to rail (118) during tightening is provided that ensures full seating of clamp (200) to rail (118) during securing clamp (200) to rail (118). For instance, the linear movement of jaw (214) to effectuate securing clamp (200) to rail (118), along with the dovetail-like shape of protrusion (134) and complementary shape of void space or shape defined by jaws (212, 214) provides that clamp (200) pulls itself toward rail (118) during tightening. This promotes that jaws (212, 214) contact rail (118) in such a way that jaws (212, 214) are aligned and therefore will fully seat when secured to rail (118). This configuration further provides for a repeatable closure of clamp (200), and when secured to rail (118), the connection between clamp (200) and rail (118) is repeatable and stable.

Exemplary Navigation Adapter

Figure 13:
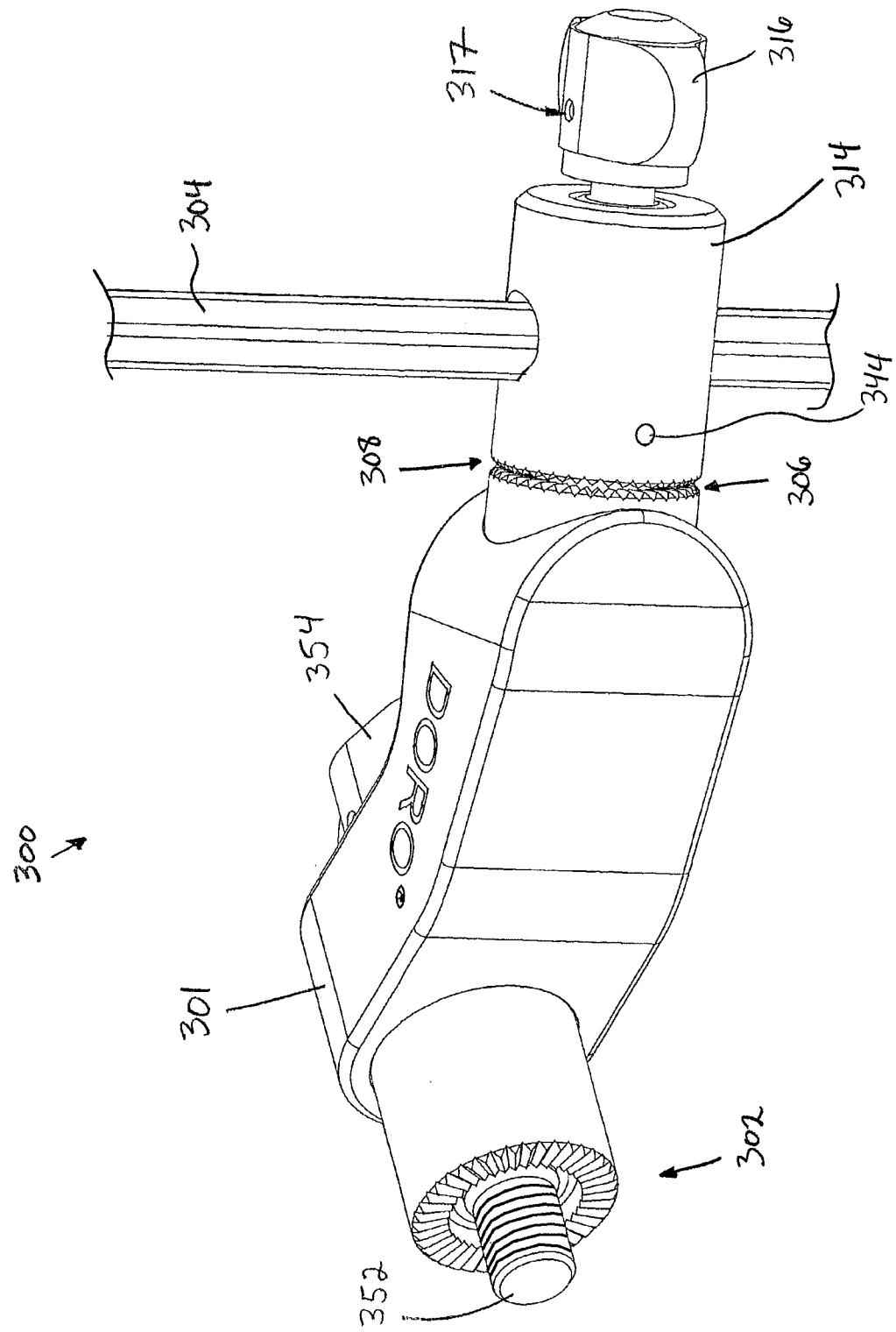
FIG. 13 depicts a magnified perspective view of the navigation adapter of FIG. 1.
Figure 14:
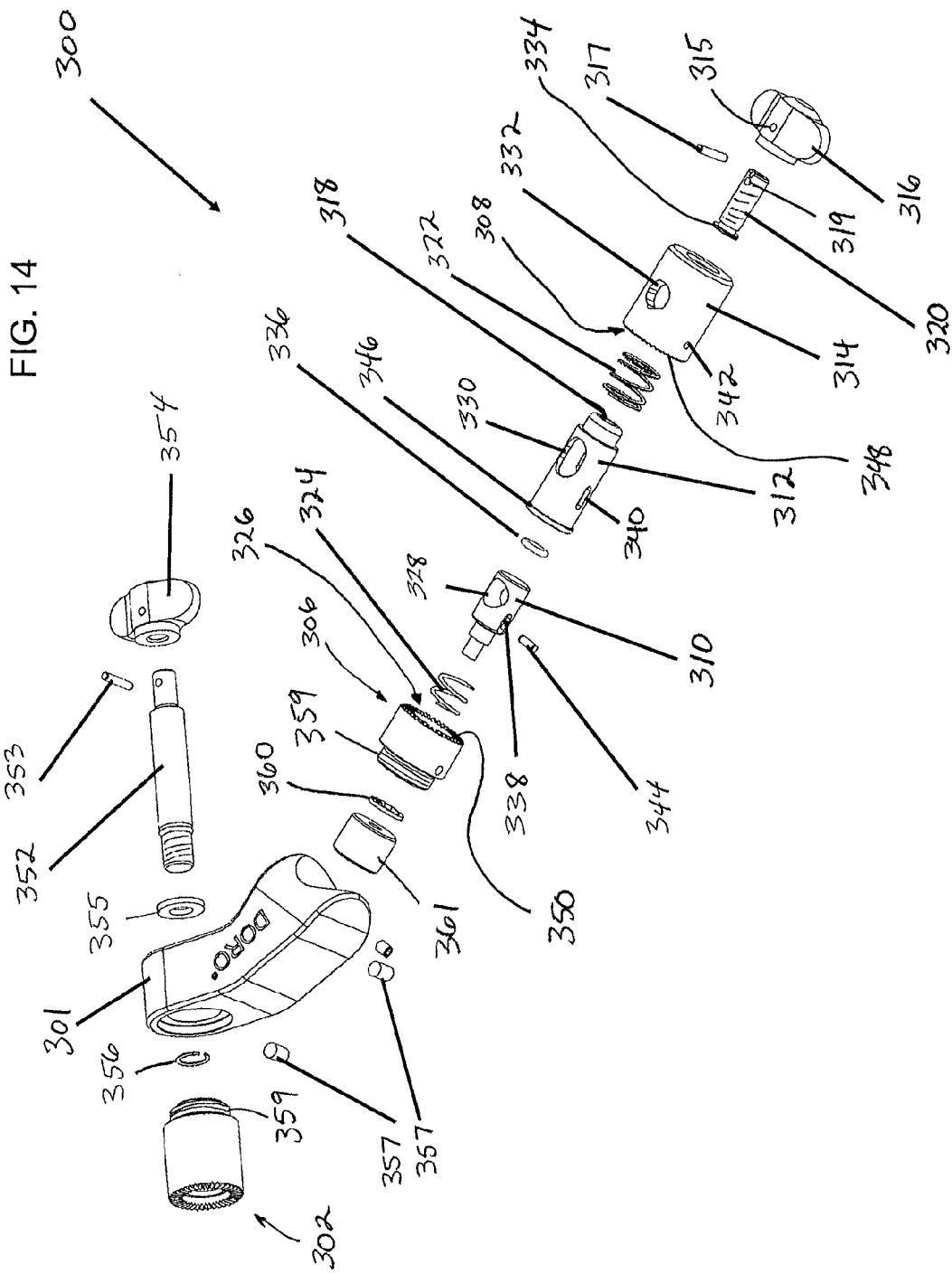
FIG. 14 depicts an exploded view shown in perspective of the navigation adapter of FIG. 1, shown without the long post and components attached thereto.
Figure 15:
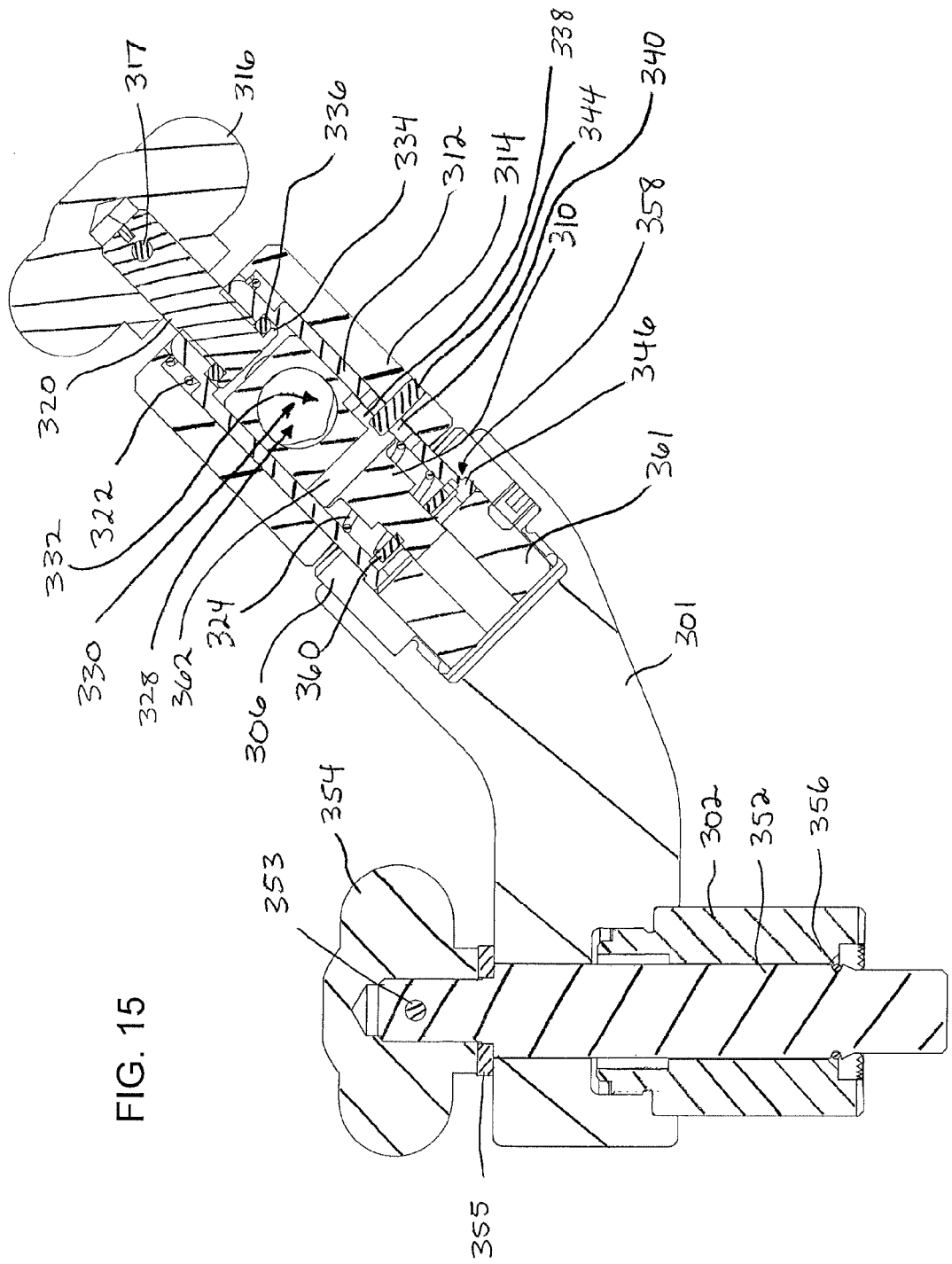
FIG. 15 depicts a top view, shown in cross section, of the navigation adapter of FIG. 1, shown without the post.

FIGS. 13-15 illustrate an exemplary navigation adapter (300) comprising body (301). In the present example, navigation adapter (300) connects with rail (118) of HFD (10) at one end via starburst interface (302) and complementary starburst interface (124) as described above. Associated with starburst interface (302), as shown in FIG. 14 are threaded rod (352), pin (353), actuator (354), and washers (355, 356). Actuator (354) is configured to rotate in unison with threaded rod (352), which engages threaded bore (128) of starburst interface (124) to draw the teeth of starburst interfaces (302, 124) together. The engagement between starburst interfaces (302, 124) selectively secures navigation adapter (300) to HFD (10). When the engagement between starburst interfaces (302, 124) is sufficiently loose, navigation adapter (300) can be rotated about starburst interfaces (302, 124) to orient navigation adapter (300) in a desired position. Thus, the connection between starburst interfaces (124, 302) provides navigation adapter (300) with a first axis of rotation for adjusting the position of navigation adapter (300) relative to skull clamp (100).

At the other end of navigation adapter (300), navigation adapter is configured to retain a tracking device (400) (also at times referred to as a reference device or a reference marker) supported by post (304). Post (304) comprises connector (305) at the top, and connector (305) connects with the tracking device (400). Generally, tracking devices are configured to provide spatial data by serving as a reference to any instrument or marker that may be used in conjunction with navigation systems. For instance, tracking device (400) can be configured to be maintained in the same location throughout a procedure as an instrument or marker moves within the three dimensional space. With such navigation systems, both tracking device (400) and any instrument or marker used in the procedure are communicating with the navigation system. Post (304) is adjustable vertically relative to a longitudinal axis defined by body (301) of navigation adapter (300). Also, post (304) can be adjusted rotationally via starburst interfaces (306, 308) that join the portion of navigation adapter (300) that retains post (304) with the remainder of navigation adapter (300). Thus, the connection between starburst interfaces (306, 308) provides navigation adapter (300) with a second axis of rotation for adjusting the position of navigation adapter (300) relative to skull clamp (100). In the present example, as described further below, post (304) is adjustable vertically and rotationally by manipulating a single actuator (316).

As also illustrated in FIGS. 13-15, body (301) of navigation adapter (300) comprises pins (357) that retain certain portions of navigation adapter (300) within body (301). For instance, pins (357) function to retain starburst interfaces (302) and (306) within body (301) of navigation adapter (300). In some versions starburst interfaces (302, 306) comprise threaded ends (359) that engage body (301) with a threaded engagement instead of or in addition to being retained by pins (357).

Referring to FIGS. 14-15, the portion of navigation adapter (300) that retains post (304) comprises inner body (310), middle body (312), outer body (314), and actuator (316). Inner body (310) fits within middle body (312) and those fit within outer body (314) such that openings (328, 330, 332) for post (304) can be aligned. Middle body (312) includes threaded bore (318) configured to engage with the threads on threaded rod (320), which connects to actuator (316). Threaded rod (320) comprises flange (334), and when assembled, flange (334) is adjacent o-ring (336) within middle body (312) as best seen in FIG. 15. Thus when assembled, threaded rod (320) is inserted through middle body (312) and outer body (314) from the end closest to starburst interface (306). Threaded rod (320) is held within actuator (316) by pin (317) that extends through bore (315) of actuator (316) and bore (319) in threaded rod (320) such that rotation of actuator (316) produces corresponding rotation of threaded rod (320).

First spring (322) is positioned between one end of middle body (312) and outer body (314) as shown in FIGS. 14 and 15. Second spring (324) is positioned between the end of inner body (310) nearest starburst interface (306) and extends within interior bore (326) of starburst interface (306) abutting ring (360). Inner body (310) and middle body (312) are configured with lateral slots (338, 340) while outer body (314) includes lateral bore (342). Pin (344) connects with bore (342) of outer body (314) and extends through slots (338, 340) of middle body (312) and inner body (310). In the present example, lateral slot (338) of inner body (310) is configured with an intersecting bore (362) that extends laterally through inner body (310). In some versions, when pin (344) seats within slot (338), pin (344) can extend at least partially or be extended at least partially within intersecting bore (362). In some other versions, when pin (344) seats within slot (338), pin (344) extends only within the lateral portion of slot (338) and not within intersecting bore (362). As discussed further below, in some versions lateral movement of inner body (310) will produce lateral movement of pin (344) by pin (344) contacting a portion of lateral slot (338) that is closest to threaded rod (320) after sufficient lateral movement of inner body (310). Furthermore, lateral movement of pin (344) will produce lateral movement of outer body (314) since pin (344) engages bore (342) when navigation adapter (300) is assembled. At the same time, middle body (312) remains stationary even when inner body (310), pin (344), and outer body (314) move laterally because pin (344) moves within slot (340) of middle body (312) and because of the specific configuration of middle body (312) as described further below.

When actuator (316) is rotated, threaded rod (320) engages with threaded bore (318) of middle body (312). Middle body (312) comprises flange (346) that abuts notch (358) within the sidewall of interior bore (326) of starburst interface (306). Flange (346) further abuts spacer (361) and thus middle body (312) remains stationary because of this contact between flange (346) and notch (358) on one side, and flange (346) and spacer (361) on the other side. Thus when actuator (316) is rotated, threaded rod (320) translates toward inner body (310) and drives inner body (310) toward starburst interface (306). Slot (338) in inner body (310) is sized and configured as described above so that during at least a portion of the translation or lateral movement of inner body (310), inner body (310) will drive pin (344) in the same direction, thereby moving outer body (314) in the same direction because of the engagement of pin (344) with bore (342) of outer body (314). This movement of outer body (314) is such that teeth (348) of starburst interface (308) on outer body (314) engage teeth (350) of starburst interface (306) on body (301) of navigation adapter (300). This action selectively secures the rotational position of the post-retaining portion of navigation adapter (300). To adjust the rotational position of post (304), actuator (315) rotation is reversed to drive threaded rod (320) away from inner body (310). The spring bias of springs (322, 324) then causes springs (322, 324) to disengage starburst interface (308) from starburst interface (306) so rotational adjustment can be accomplished.

Also from rotation of actuator (316), the vertical position of post (304) is selectively secured. Post (304) extends through generally concentric openings (328, 330, 332) in inner body (310), middle body (312), and outer body (314) respectively. As inner body (310) and outer body (314) translate, post (304) is pushed in the same direction as the translation. Middle body (312) remains stationary as does its oblong shaped opening (330) through which post (304) passes. Therefore, the translation of inner body (310) and outer body (314) push post (304) against the side of opening (330) in middle body (312) that is closest to body (301) of navigation adapter (300). At the same time, post (304) is pushed from the opposite side by its contact with openings (328, 332) of inner body (310) and outer body (314) respectively. These forces and contact create an interference fit or connection between post (304) and openings (328, 330, 332) in inner body (310), middle body (312), and outer body (314) respectively, such that the vertical position of post (304) is selectively secured. The reverse motion of actuator (316) will cause the components to resiliently move back due to the spring bias of springs (322, 324), and then vertical adjustment of post (304) can be accomplished.

Referring back to FIGS. 1 and 2, and in particular to the illustration of navigation adapter (300) and starburst interface (124), the present version shows that the interface for connecting navigation adapter (300) to HFD (10)—in this case starburst interface (124)—is positioned relatively close to the skull pin assembly (110) and associated skull pins (114) that would ultimately engage a patient's head. In other words, the interface for the navigation adapter (300) is close to the structures that will be used to stabilize the patient's head. Thus the interface and the configuration of navigation adapter (300) itself are such that navigation adapter (300) can be positioned close to a patient's head, while not interfering with the structures that will be used to stabilize the patient's head or the operation of those structures. As illustrated in FIG. 1, navigation adapter (300) is positionable such that it angles away from the skull clamp (100) such that navigation adapter (300) is generally not coplanar with either skull pin assemblies (110) or arms (102) of skull clamp (100). This contributes to navigation adapter (300) not interfering with such components of skull clamp (100) like skull pin assemblies (110), clamps (200), and other components.

Additionally, incorporating starburst interface (124) relatively near the upper portion of arm (102), allows the components of attached navigation adapter (300) to extend for a shorter distance to appropriately position tracking device (400). In other words, the distance through navigation adapter (300) itself, from the starting point at the connection with starburst (124) to the ending point at connector (305) or tracking device (400), is less or shorter than this distance with other configurations where a navigation adapter attaches lower on the skull clamp (100). For instance, in other examples where a navigation adapter connects to starburst (108), the components of that navigation adapter extend for a longer distance to ultimately position tracking device (400) appropriately near the patient's head. In other words, the distance through that navigation adapter itself, from the starting point at the connection with starburst (108) to the ending point at connector (305) or tracking device (400), is greater or longer than this distance with the configuration in the illustrated version where navigation adapter (300) attaches higher on skull clamp (100) via starburst interface (124). By way of example only, and not limitation, depending on the type of tracking device used, in some versions navigation adapter (300) ranges between about 15 to 25 centimeters in cumulative length through navigation adapter (300) as described above.

Regarding construction materials, the components described herein can be made of imagining compatible materials, like aluminum or titanium among others. Of course where imaging is not a concern, the components can be made of other metals that would not necessarily be compatible with imaging modalities. Still yet, the components in some versions are made of radiolucent materials to not only be compatible with imaging modalities, but also provide little or no artifacts or imaging signature when imaging is performed. In view of the teachings herein, other materials of construction for the components described will be apparent to those of ordinary skill in the art.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of any claims that may be presented and is understood not to be limited to the details of structure and operation shown and described in the specification and drawings.

I claim:

1. A head fixation device for use in a medical procedure, wherein the head fixation device comprises:
    a. a pair of arms defining a skull clamp, wherein each of the arms comprise a cross-sectional profile that defines a rail; and
    b. at least one clamp, wherein the clamp comprises at least one movable jaw that translates linearly to selectively secure the clamp to the rail by grasping the rail, wherein the clamp selectively receives one or more accessories for use during the medical procedure.

2. The device of claim 1, wherein each arm comprises an upright portion and a lateral portion, wherein the cross-sectional profile that defines the rail extends substantially along the upright portion.

3. The device of claim 1, wherein the rail is substantially straight.

4. The device of claim 1, wherein the rail comprises at least one protruding member, wherein the clamp is securable to the rail by grasping the at least one protruding member.

5. The device of claim 4, wherein the clamp comprises an inner surface, and wherein the protruding member comprises an outer surface, wherein the inner surface of the clamp is configured to substantially contact the outer surface of the protruding member when the clamp is secured to the rail.

6. The device of claim 4, wherein the clamp comprises at least two jaws, wherein the jaws of the clamp are adjustable to define a space having a shape that matches the cross-sectional profile of the arms defining the rail.

7. The device of claim 1, wherein the clamp comprises a rail configured to receive the one or more accessories for use during the medical procedure.

8. The device of claim 1, wherein the clamp comprises at least a three point fixation with the rail when the clamp is secured to the rail.

9. The device of claim 1, wherein translation of the movable jaw is initiated by rotating a stationary rod.

10. A head fixation device for use in a medical procedure, wherein the head fixation device comprises:
    a. a pair of arms defining a skull clamp, wherein each of the pair of arms comprise an upright portion;
    b. a skull pin assembly connectable to the upright portion of a select one of the pair of arms defining the skull clamp, wherein the skull pin assembly comprises one or more skull pins that selectively contact a patient's head;

c. an integrated accessory attachment interface that selectively receives a first accessory for use during the medical procedure, wherein the integrated accessory attachment interface is positioned along the upright portion of the select one of the pair of arms defining the skull clamp having the skull pin assembly, wherein the integrated accessory attachment interface is positioned substantially proximal to the skull pin assembly having the one or more skull pins that selectively contact the patient's head.

11. The device of claim 10, wherein each of the arms comprise a cross-sectional profile that defines a rail, wherein the rail comprises:
 a. at least one protruding member; and
 b. the accessory attachment interface;
wherein the protruding member is configured to receive a second accessory for use during the medical procedure.

12. The device of claim 10, wherein the accessory attachment interface comprises a starburst interface.

13. The device of claim 10, wherein the rail comprises an outer surface, wherein the accessory attachment interface is located on the outer surface of the rail.

14. The device of claim 10, wherein the first accessory is a navigation adapter.

15. The device of claim 14, wherein the navigation adapter extends outward from the rail such that the navigation adapter is generally not coplanar with the stabilizing feature.

16. The device of claim 14, wherein the navigational adapter is adjustable about two axes of rotation and further is adjustable vertically relative to a longitudinal axis defined by a body of the navigation adapter.

17. The device of claim 10, wherein the first accessory comprises at least one axis of rotation for rotational adjustment, and wherein the first accessory further comprises an interface for a navigation accessory for use during the medical procedure.

* * * * *